United States Patent
Fujita et al.

(10) Patent No.: US 11,384,372 B2
(45) Date of Patent: Jul. 12, 2022

(54) METHOD FOR PRODUCING INOSITOL DERIVATIVE

(71) Applicant: SHOWA DENKO K.K., Tokyo (JP)

(72) Inventors: Ichiro Fujita, Kawasaki (JP); Shinji Yamaki, Kawasaki (JP)

(73) Assignee: SHOWA DENKO K.K., Tokyo (JP)

( * ) Notice: Subject to any disclaimer, the term of this patent is extended or adjusted under 35 U.S.C. 154(b) by 37 days.

(21) Appl. No.: 16/641,871

(22) PCT Filed: Sep. 4, 2018

(86) PCT No.: PCT/JP2018/032682
§ 371 (c)(1),
(2) Date: Feb. 25, 2020

(87) PCT Pub. No.: WO2019/045112
PCT Pub. Date: Mar. 7, 2019

(65) Prior Publication Data
US 2020/0248219 A1  Aug. 6, 2020

(30) Foreign Application Priority Data

Sep. 4, 2017 (JP) .............................. JP2017-169773

(51) Int. Cl.
*C12P 19/14* (2006.01)
*C12P 19/02* (2006.01)
*C12P 19/18* (2006.01)

(52) U.S. Cl.
CPC .............. *C12P 19/02* (2013.01); *C12P 19/18* (2013.01)

(58) Field of Classification Search
CPC .......................... C12P 19/14; C12Y 204/01019
See application file for complete search history.

(56) References Cited

U.S. PATENT DOCUMENTS 4,477,568 A * 10/1984 Hokse ................. C08B 37/0012
                                                            435/197
5,376,537 A    12/1994 Cami et al.
5,492,829 A *  2/1996 Choi ...................... C12N 1/205
                                                            435/252.1

FOREIGN PATENT DOCUMENTS

| JP | 63-133998 A | 6/1988 |
| JP | 63-196596 A | 8/1988 |
| JP | 01-179698 A | 7/1989 |
| JP | 09-3089 A | 1/1997 |
| JP | 4624831 B2 | 2/2011 |
| WO | 2005092285 A1 | 10/2005 |

OTHER PUBLICATIONS

Sato et al., Biotechnol. Lett., 14(8), 659-664, 1992.*
International Search Report of PCT/JP2018/032682 dated Oct. 16, 2018 [PCT/ISA/210].
Communication dated May 6, 2021, from the European Patent Office in application No. 18850558.0.

* cited by examiner

*Primary Examiner* — Maryam Monshipouri
(74) *Attorney, Agent, or Firm* — Sughrue Mion, PLLC

(57) ABSTRACT

A method for producing an inositol derivative includes a step of reacting inositol and dextrin in the presence of cyclodextrin glucanotransferase to generate an inositol derivative in which a sugar is bonded to the inositol, and to obtain a solution containing the inositol derivative and the cyclodextrin glucanotransferase; and a step of removing the cyclodextrin glucanotransferase in the solution using an ultrafiltration membrane, in which a deactivation treatment of the cyclodextrin glucanotransferase in the solution is not performed.

7 Claims, No Drawings

METHOD FOR PRODUCING INOSITOL DERIVATIVE

CROSS REFERENCE TO RELATED APPLICATIONS

This application is a National Stage of International Application No. PCT/JP2018/032682, filed Sep. 4, 2018, claiming priority to Japanese Patent Application No. 2017-169773, filed Sep. 4, 2017.

TECHNICAL FIELD

The present invention relates to a method for producing an inositol derivative.
Priority is claimed on Japanese Patent Application No. 2017-169773, filed Sep. 4, 2017, the content of which is incorporated herein by reference.

BACKGROUND ART

Inositol derivatives in which a sugar group is bonded to inositol are known to exhibit an effect of moisturizing skin and keeping skin healthy (Patent Literature 1). As a method of synthesizing such inositol derivatives, a method is known in which inositol and cyclodextrin, which is a kind of oligosaccharide, are reacted in the presence of cyclodextrin glucanotransferase (hereinafter referred to as "CGTase") to obtain a sugar or oligosaccharide to which the inositol residue is bonded (Patent Literature 2).

As a method of deactivating an enzyme after an enzyme reaction is completed in the enzyme reaction using CGTase, a method of heating a reaction solution, or a method of adding chemicals such as an acidic chemical or an alkaline chemical is generally used. For example, in Patent Literature 1 and Patent Literature 2, inositol and cyclodextrin are reacted in the presence of CGTase, and then the reaction solution is boiled, thereby deactivating the enzyme.

Meanwhile, a method of recovering a product without deactivating an enzyme in an enzyme reaction using CGTase is also known. For example, Patent Literature 3 discloses that, in a method for producing cyclodextrin by allowing CGTase to act on starch, cyclodextrin is separated from a reaction system by an ultrafiltration method. In addition, Patent Literature 4 discloses that CGTase is allowed to act on a substrate formed of a mixture of starch and sucrose, and maltooligosaccharose thus generated is separated off using an ultrafiltration membrane.

CITATION LIST

Patent Literature

[Patent Literature 1]
Japanese Patent No. 4624831
[Patent Literature 2]
Japanese Unexamined Patent Application, First Publication No. S63-196596
[Patent Literature 3]
Japanese Unexamined Patent Application, First Publication No. S63-133998
[Patent Literature 4]
Japanese Unexamined Patent Application, First Publication No. H1-179698

SUMMARY OF INVENTION

Technical Problem

However, in a case where an enzyme is deactivated by heating or adding a chemical, contamination with a denatured product of the enzyme component, and coloration or alteration of inositol derivatives that are products, may occur. In addition, a method of separating an active enzyme using an ultrafiltration membrane as in Patent Literature 3 and Patent Literature 4 is performed simply for the purpose of removing the enzyme from a reaction solution, and improving the degree of purification of a product is not taken into consideration. In addition, there is a risk of overreaction due to an active enzyme.

Accordingly, an object of the present invention is to provide a method for producing an inositol derivative in which an active enzyme is removed without altering the inositol derivative that is the product, thereby improving the degree of purification of the inositol derivative and obtaining a high-quality inositol derivative.

Solution to Problem

The present invention includes the following aspects.
(1) A method for producing an inositol derivative including a step of reacting inositol and dextrin in the presence of cyclodextrin glucanotransferase to generate an inositol derivative in which a sugar is bonded to the inositol, and to obtain a solution containing the inositol derivative and the cyclodextrin glucanotransferase; and a step of removing the cyclodextrin glucanotransferase in the solution using an ultrafiltration membrane, in which a deactivation treatment of the cyclodextrin glucanotransferase in the solution is not performed.
(2) The method for producing an inositol derivative according to (1), in which a molecular weight cut-off of the ultrafiltration membrane is 1,000 to 100,000.
(3) The method for producing an inositol derivative according to (1) or (2), in which the removal of the cyclodextrin glucanotransferase using the ultrafiltration membrane is performed under a temperature condition of 0° C. to 60° C.
(4) The method for producing an inositol derivative according to any one of (1) to (3), in which the removal of the cyclodextrin glucanotransferase using the ultrafiltration membrane is performed by cross-flow ultrafiltration.
(5) The method for producing an inositol derivative according to any one of (1) to (4), in which the reaction of reacting the inositol with the dextrin is performed under a condition in which a temperature is 20° C. to 80° C. and a pH is 3 to 9.
(6) The method for producing an inositol derivative according to any one of (1) to (5), in which the dextrin is β-cyclodextrin.
(7) The method for producing an inositol derivative according to any one of (1) to (6), in which the inositol is myo-inositol.

Advantageous Effects of Invention

According to the present invention, a method for producing an inositol derivative is provided by which a high-quality inositol derivative with a high degree of purification can be obtained.

DESCRIPTION OF EMBODIMENTS

In one embodiment, the present invention provides a method for producing an inositol derivative, the method including a step of reacting inositol and dextrin in the presence of cyclodextrin glucanotransferase to generate an inositol derivative in which a sugar is bonded to the inositol, and to obtain a solution containing the inositol derivative and the cyclodextrin glucanotransferase (hereinafter referred to as the "Step I"); and a step of removing the cyclodextrin glucanotransferase in the solution using an ultrafiltration membrane (hereinafter referred to as the "Step II"), in which a deactivation treatment of the cyclodextrin glucanotransferase in the solution is not performed.

Hereinafter, each of these steps will be described.

[Step I]

Step 1 is a step of reacting inositol and dextrin in the presence of cyclodextrin glucanotransferase (CGTase) to generate an inositol derivative in which a sugar is bonded to the inositol, and to obtain a solution containing the inositol derivative and CGTase.

(Inositol)

Inositol is a cyclic hexahydric alcohol represented by $C_6H_6(OH)_6$. There are nine stereoisomeric forms of inositol: cis-inositol, epi-inositol, allo-inositol, myo-inositol, muco-inositol, neo-inositol, chiro-inositol (D-chiro- and L-chiro-), and scyllo-inositol.

The inositol used in the present step is preferably myo-inositol which is physiologically active among the above-mentioned isomeric forms. Inositol can be synthesized by a method of extraction from rice bran, a chemical synthesis method, a fermentation method, or the like. In addition, a commercially available product may also be used. The structural formula of myo-inositol is shown below.

[Chem. 1]

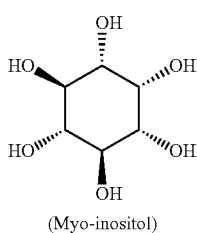

(Myo-inositol)

(Dextrin)

Dextrin is a generic term applied to products obtained by reducing the molecular weight of starch by chemical or enzymatic methods.

The dextrin used in the present step is not particularly limited, but from the viewpoint of efficiency of generating the inositol derivative, for example, dextrin in which a content of dextrin having a degree of polymerization of 7 or more is 85% by mass or more, is preferably 90% by mass or more, and is more preferably 98% by mass or more, may be used.

In addition, the dextrin is preferably a cyclodextrin from the viewpoint of efficiency of generating the inositol derivative. Cyclodextrins are cyclic oligosaccharides having a cyclic structure in which D-glucose units are bonded by α-1,4-glycosidic bonds. The cyclodextrin is not particularly limited, and examples thereof include α-cyclodextrin, β-cyclodextrin, γ-cyclodextrin, and the like. Among these, β-cyclodextrin is preferably used because it is industrially inexpensive and can be stably supplied.

Dextrin can be obtained by reducing the molecular weight of starch by chemical or enzymatic methods. In addition, cyclodextrin can be obtained by allowing cyclodextrin glucanotransferase to act on starch. A commercially available dextrin or cyclodextrin may be used.

(Inositol Derivative)

The inositol derivative produced by the production method of the present embodiment is an inositol derivative in which a sugar is bonded to inositol. In the inositol derivative, a sugar is bonded to a hydroxyl group of inositol. The sugar may be bonded to any one of six hydroxyl groups present in an inositol molecule, or may be bonded to any two or more thereof.

In the inositol derivative produced by the production method of the present embodiment, the sugar that is bonded to inositol is a glucose or an oligosaccharide containing glucose as structural units. For example, one or more glucose may be bonded to one inositol molecule, one or more oligosaccharides may be bonded to one inositol molecule, or one or more glucose and one or more oligosaccharides may be bonded to one inositol molecule. In the inositol derivative, a total number of glucose or oligosaccharides bonded to one inositol molecule in terms of monosaccharide units is 1 or more, may be 2 or more for example, may be 3 or more for example, and may be 4 or more for example.

In the present specification, a monosaccharide refers to a sugar group that cannot be hydrolyzed further, and refers to a compound that is a constituent element when forming a polysaccharide. A monosaccharide can also be said to be the smallest structural unit of a sugar group. In the present specification, the term "monosaccharide unit" refers to a chemical structure corresponding to a monosaccharide. A "monosaccharide unit" can also be said to be a chemical structure derived from a monosaccharide. For example, a disaccharide is converted into two monosaccharide units, and a trisaccharide is converted into three monosaccharide units. For example, α-cyclodextrin is converted into six monosaccharide units; β-cyclodextrin is converted into seven monosaccharide units; and γ-cyclodextrin is converted into eight monosaccharide units.

The inositol derivative produced by the production method of the present embodiment may be a mixture of inositol derivatives in which different numbers of sugars are bonded to inositol in terms of monosaccharide units. For example, the inositol derivative may be a mixture of an inositol derivative in which one saccharide in terms of monosaccharide units is bonded to one inositol molecule, an inositol derivative in which two saccharides in terms of monosaccharide units are bonded to one inositol molecule, an inositol derivative in which three saccharides in terms of monosaccharide units are bonded to one inositol molecule, an inositol derivative in which four saccharides in terms of monosaccharide units are bonded to one inositol molecule, and an inositol derivative in which five or more saccharides in terms of monosaccharide units are bonded to one inositol molecule.

(Cyclodextrin Glucanotransferase: CGTase)

CGTase is an enzyme catalyzing a reaction in which an α-1,4-glucoside bond is formed to cyclize an α-1,4-glucan chain. CGTase acts on a substrate having an α-1,4-glucan chain, such as starch, to generate cyclodextrin. As CGTases, CGTases derived from bacteria such as the genus *Bacillus*, the genus *Brevibacterium*, the genus *Clostridium*, the genus *Corynebacterium*, the genus *Klebsiella*, the genus *Micrococcus*, the genus *Thermoanaerobacter*, and the genus *Thermoanaerobacterium* are known currently.

When inositol and dextrin are reacted in the presence of CGTase, CGTase acts on the dextrin, and transfer of glucose residues occurs with the inositol as an acceptor, thereby generating inositol derivatives.

CGTase used in the present step is not particularly limited as long as it can generate the above-mentioned inositol derivatives from inositol and dextrin. CGTases derived from bacteria as described above may be used, or CGTases obtained by modifying these natural CGTases may be used. Examples of CGTase include CGTases disclosed in Japanese Unexamined Patent Application, First Publication No. S63-196596 and PCT International Publication No. WO96/33267, and the like, but examples are not limited thereto. A commercially available CGTase may be used.

(Reaction of Generating Inositol Derivatives)

The reaction in which inositol and dextrin are reacted in the presence of CGTase to generate an inositol derivative in which a sugar is bonded to inositol (hereinafter referred to as the "inositol derivatives generation reaction") can be performed using a method used in general enzyme reactions without particular limitation. Specifically, the inositol derivatives generation reaction can be performed by mixing inositol, dextrin, and CGTase in a suitable solvent, and allowing certain time to pass.

In the inositol derivatives generation reaction, as a solvent in which the substrate and CGTase are mixed, a buffer solution used for general enzyme reactions can be used without particular limitation. Examples of such buffer solutions include a citrate buffer solution, a phosphate buffer solution, a Tris-HCl buffer solution, a HEPES buffer solution, and the like, but examples are not limited thereto.

A mixing ratio between inositol and dextrin is not particularly limited, and it may be appropriately set according to the type of inositol derivative to be produced. As the proportion of inositol becomes higher, the number of monosaccharide units of sugar bonded per inositol molecule becomes smaller. In contrast, as the proportion of dextrin becomes higher, the number of monosaccharide units of sugar bonded per inositol molecule becomes larger.

For example, a mass ratio between dextrin to inositol (dextrin/inositol) can be 1 to 12, and it is preferably 2 to 6 and more preferably 3 to 5.

A concentration of inositol in a reaction solution is not particularly limited, but from the viewpoint of improving a batch production amount and avoiding a long reaction time, for example, the concentration thereof is 1 to 400 g/L, and it is preferably 10 to 300 g/L and more preferably 50 to 200 g/L.

A concentration of dextrin in a reaction solution is not particularly limited, but from the viewpoint of maintaining reaction efficiency and reducing production costs, for example, the concentration thereof is 10 to 1500 g/L, and it is preferably 100 to 1000 g/L and more preferably 200 to 800 g/L.

Regarding a method of adding the dextrin, the dextrin may be added initially all at once or may be added after the initial addition. In the case of adding dextrin later, a timing of addition is not particularly limited, and examples thereof include after 4 hours, 8 hours, and 11 hours from the start of the reaction. Dextrin is preferably added all at once.

A concentration of CGTase in a reaction solution is not particularly limited, but for example, it is 0.01 to 100 g-SS/L, is preferably 0.05 to 50 g-SS/L, and is more preferably 0.1 to 10 g-SS/L.

Reaction conditions at the time of the inositol derivatives generation reaction may be suitably set according to the type of CGTase. In a case of using a commercially available CGTase, reaction conditions can be set according to recommended conditions of the manufacturer. For example, a reaction temperature is 20° C. to 80° C., is preferably 30° C. to 70° C., and is more preferably 40° C. to 60° C. For example, a reaction pH is pH 3 to pH 9, is preferably pH 4 to pH 8, and is more preferably pH 5 to pH 7. In a case where the reaction temperature and pH are within these ranges, an enzyme activity of CGTase can be maintained in a high state.

A reaction time of the inositol derivatives generation reaction is not particularly limited, and it may be suitably set according to the type of CGTase, an amount of a reaction solution, and the like. From the viewpoint of efficiency of generating inositol derivatives and inhibiting production of residual unreacted products, for example, the reaction time is 5 to 300 hours, is preferably 30 to 70 hours, and is more preferably 40 to 60 hours. For example, the reaction may be performed until disappearance of dextrin can be confirmed by measuring the concentration of dextrin in the reaction solution by HPLC, LC-MS, or the like.

By performing the inositol derivatives generation reaction in the manner described above, an inositol derivative is generated in the reaction solution, and thereby it is possible to obtain a solution containing the inositol derivative and CGTase (hereinafter referred to as the "inositol derivative/CGTase solution"). The inositol derivative generated in the present step is generally a mixture of inositol derivatives in which different numbers of sugars are bonded to inositol in terms of monosaccharide units.

[Step II]

Step II is a step of removing CGTase in the solution containing the inositol derivative and CGTase, which is obtained in Step I, using an ultrafiltration membrane.

In the present step, ultrafiltration is performed using the inositol derivative/CGTase solution obtained in Step I as a feed solution. In the production method of the present embodiment, the deactivation treatment of CGTase is not performed after Step I. After the inositol derivatives generation reaction, by removing CGTase into a concentrate using an ultrafiltration membrane without performing the deactivation treatment of CGTase, it is possible to obtain a high-quality inositol derivative with a high degree of purification while avoiding alteration of the inositol derivative recovered in a filtrate. In the present specification, a "feed solution" refers to a liquid to be subjected to ultrafiltration, a "filtrate" refers to a liquid that has passed through an ultrafiltration membrane, and a "concentrate" refers to a liquid that has not passed through an ultrafiltration membrane.

The ultrafiltration membrane used in the present step is not particularly limited, but an ultrafiltration membrane that can be used for cross-flow ultrafiltration is preferable. In cross-flow ultrafiltration, a feed solution, which is subject to filtration, is allowed to flow parallel to a membrane surface of the ultrafiltration membrane. Accordingly, solute molecules smaller than the pore size of the ultrafiltration membrane and some of the feed solution become a filtrate, and molecules larger than the pore size of the membrane are concentrated. Since various types of ultrafiltration membrane that can be used for cross-flow ultrafiltration are commercially available, an ultrafiltration membrane can be suitably selected among these and used.

A molecular weight cut-off of the ultrafiltration membrane used in the present step is within a range of 1000 to 100,000. In a case where the molecular weight cut-off is less than 1000, the filtration rate becomes low, causing deterioration in the efficiency in purification of inositol derivatives and productivity thereof. In a case where the molecular weight cut-off exceeds 100,000, there is a high probability of impurities derived from CGTase being mixed into the filtrate. A molecular weight cut-off of the ultrafiltration membrane is preferably 1000 to 100,000, is more preferably 1000 to 70,000, is even more preferably 3000 to 20,000, and is particularly preferably 4000 to 15,000.

A method of ultrafiltration in the present step is not particularly limited, but it is preferably cross-flow ultrafiltration. By performing cross-flow ultrafiltration, adhesion of impurities to a surface of the ultrafiltration membrane can be reduced, and this can inhibit occurrence of clogging.

Temperature conditions at the time of the ultrafiltration can be, for example, 0° C. to 60° C., and it is preferably a temperature lower than the reaction temperature in Step I. In a case where the temperature is equal to or higher than the lower limit of the above temperature conditions, fluidity of the feed solution is maintained, and thereby filtration can be performed efficiently. In a case where the temperature is equal to or lower than the upper limit of the above temperature conditions, overreaction due to CGTase in the feed solution can be inhibited. Temperature conditions at the time of the ultrafiltration are preferably 0° C. to 50° C. and more preferably 0° C. to 40° C.

In the production method of the present embodiment, since the deactivation treatment of CGTase is not performed after Step I, addition of an acidic chemical, an alkaline chemical, or the like to a solution after the reaction is not necessary. For this reason, a pH of the feed solution at the time of ultrafiltration does not significantly differ from a pH of the reaction solution in Step I. For example, a pH of the feed solution at the time of ultrafiltration is pH 3 to pH 9.

By performing ultrafiltration using the ultrafiltration membrane as described above and using the solution containing the inositol derivative and CGTase which is obtained in Step 1 as the feed solution, CGTase and impurities derived therefrom remain in the concentrate, whereas the inositol derivative transfers to the filtrate.

Accordingly, by recovering the filtrate, it is possible to obtain inositol derivatives with a high degree of purification which does not contain CGTase and impurities derived therefrom.

It is preferable that CGTase activity be not detected in an ultrafiltration filtrate obtained in the present step. Detection of CGTase activity in the filtrate can be performed by, for example, collecting some of the filtrate, adding inositol (for example, myo-inositol) to a final concentration of 10 g/L, reacting the mixture at 50° C. for 1 hour or longer, and thereafter, measuring a content of inositol in the liquid.

A content of inositol can be measured using, for example, high-performance liquid chromatography. In a case where there is no substantial difference in content of inositol between before and after the reaction, it can be determined that CGTase activity has not been detected. The term "no substantial difference" means that, for example, a difference in content of inositol detected between before and after the reaction is about 5% or less with respect to a content of inositol detected before the reaction (100%). The difference in content of inositol is preferably 3% or less, is more preferably 2% or less, and is even more preferably 1% or less.

A total content of CGTase and impurities derived therefrom (soluble peptides) in a purified product of the inositol derivative which is obtained after the present step can be, for example, 3% by mass or less. The total content can be preferably 1% by mass or less and can be more preferably 0.5% by mass or less.

The production method of the present embodiment is characterized in that the deactivation treatment of CGTase in the inositol derivative/CGTase solution obtained in Step I is not performed. In the present specification, the "deactivation treatment" refers to treatment of denaturing CGTase through heating or chemical treatment to allow CGTase to lose its enzyme activity. An enzyme activity after the deactivation treatment is preferably 30% or less, is more preferably 20% or less, is even more preferably 10% or less, and is particularly preferably 5% or less of an enzyme activity before the deactivation treatment. Examples of deactivation treatment include heat treatment (for example, 70° C. or higher), acid treatment (for example, pH 2 or lower), alkali treatment (for example, pH 10 or higher), and organic solvent treatment (for example, phenol and chloroform). In the production method of the present embodiment, alteration of the inositol derivative in the inositol derivative/CGTase solution can be prevented by not performing the deactivation treatment of CGTase.

By performing ultrafiltration using the inositol derivative/CGTase solution as a feed solution without performing the deactivation treatment of CGTase, it is possible to obtain a transparent filtrate with almost no turbidity and coloration in the present step. For example, OD660, OD440, and OD280 of the filtrate can be respectively indicative of turbidity, coloration, and a content of soluble peptides. OD660 of the ultrafiltration filtrate in the present step may be 0.01 or less and is preferably 0.008 or less per 1 g of a solid content in the filtrate. OD440 of the filtrate may be 0.02 or less, is preferably 0.019 or less, is more preferably 0.016 or less, and is even more preferably 0.015 or less per 1 g of a solid content in the filtrate. OD280 of the filtrate may be 4.0 or less, is preferably 3.8 or less, is more preferably 3.7 or less, and is even more preferably 3.6 or less per 1 g of a solid content in the filtrate.

Respective OD values per 1 g of a solid content of the filtrate can be obtained by measuring absorbances of the filtrate at 660 nm, 440 nm, and 280 nm, and dividing the measured value by a concentration of solid contents of the filtrate. Regarding OD440 and OD280, an ultrafiltration filtrate is filtered with a 0.45-μm membrane filter, and the absorbance of the obtained filtrate is measured. A concentration of solid contents of the ultrafiltration filtrate can be obtained by, for example, measuring an amount of residue on evaporation of the filtrate using a Kett type moisture meter under a condition of 105° C. for 60 minutes.

[Other Steps]

The production method of the present embodiment may include other steps in addition to Steps I and II. Examples of other steps include various steps generally used as a means for purifying chemical substances, a step of analyzing the type of inositol derivative, a step of separating an inositol derivative according to numbers of monosaccharide units of a sugar bonded to inositol, and the like. These other steps can be performed using known methods. For example, a white powder of an inositol derivative can be obtained by performing freeze-drying or spray-drying of the obtained filtrate after Step II.

Although the production method of the present embodiment may include other steps between Step I and Step II, it is preferable to perform Step II immediately after Step I from the viewpoint of preventing overreaction due to CGTase. Even in a case where the production method of the present embodiment includes other steps, the production method does not include a step of performing the deactivation treatment of CGTase in these other steps.

In the production method of the present embodiment, since CGTase is not deactivated, the inositol derivative can be prevented from being altered due to the deactivation treatment. By removing CGTase into a concentrate using an ultrafiltration membrane after the inositol derivatives generation reaction, it is possible to obtain an inositol derivative with a high degree of purification which does not contain CGTase and impurities derived therefrom in a filtrate.

Since the inositol derivative produced by the production method of the present embodiment has a high degree of purification and has a high quality, it can be used in various applications such as cosmetic preparations, pharmaceuticals, and food products.

EXAMPLES

Hereinafter, while the present invention will be described with reference to the following experimental examples, the present invention is not limited to the following experimental examples.

[Analysis Method]
(Absorbance)

Measurement of OD660, OD440, and OD280 per 1 g of a solid content of a sample was performed by the following methods. OD660, OD440, and OD280 are respectively indicators of turbidity, coloration, and a content of soluble peptides of the sample.

Using a Kett type moisture meter (a halogen moisture meter HG63-P, manufactured by METTLER TOLEDO), an amount of residue (=100%−water content %) on evaporation of the sample was measured under conditions of 105° C. for 60 minutes. This amount was used as a concentration of solid contents (w/w %) of the sample.

OD660 was obtained by adding 3 mL or more of the sample to a 1 cm square quartz cell, and measuring the absorbance at 660 nm with a spectrophotometer (model number U-1800, manufactured by Hitachi, Ltd.).

OD440 and OD280 were obtained by filtering the sample with a 0.45-μm membrane filter, adding 3 mL of the obtained filtrate to a 1 cm square quartz cell, and measuring absorbances at 440 nm and 280 nm with a spectrophotometer (model number U-1800, manufactured by Hitachi, Ltd.).

OD660, OD440, and OD280 with respect to solid contents of the sample were respectively calculated by dividing each absorbance obtained as described above by the concentration of solid contents of the sample.

(Activity of Residual CGTase)

Myo-inositol was added to the sample to a final concentration of 10 g/L, and the mixture was reacted at 50° C. for 1 hour or longer to analyze a product before and after the reaction after adding the myo-inositol (before the reaction: immediately after adding the myo-inositol, and after the reaction: 1 hour after the reaction at 50° C.) by high-performance liquid chromatography. The analysis was performed using a Shodex high-performance liquid chromatography instrument under the following analysis conditions. In a case where a myo-inositol peak after the reaction did not change compared to that before the reaction, the activity of CGTase residue was determined to have "no activity," whereas in a case where the peak decreased, the activity of CGTase residue was determined to have "activity."

<Analysis Conditions>
Column: Shodex KS802
Eluent: water
Flow rate: 0.5 mL/min
Oven temperature: 75° C.
Detection: RI (differential refractive index)
(Analysis of Main Components)

The analysis of main components of the sample was performed using a Shodex high-performance liquid chromatography instrument under the following analysis conditions.

<Analysis Conditions>
Column: Shodex HILICpak VN-50 4D×1
Eluent: $CH_3CN$:water=60:40 (V:V)
Flow rate: 0.3 mL/min
Oven temperature: 40° C.
Detection: RI (differential refractive index)

Examples 1 to 7

Under conditions shown in Table 1, using a 5 L culture tank (model number MD-300, manufactured by Marubishi Bioengineering Co., Ltd.), myo-inositol (manufactured by Tsuno Rice Fine Chemicals Co., Ltd.) and β-cyclodextrin (manufactured by ENSUIKO Sugar Refining Co., Ltd.) were reacted in the presence of a CGTase (manufactured by Novozymes), and thereby inositol derivatives were generated. A "composition of reaction solution" in Table 1 indicates a final concentration.

TABLE 1

| Composition of reaction solution | β-cyclodextrin | 459 g/L |
|---|---|---|
| | Myo-inositol | 116 g/L |
| | CGTase | 0.5 g-SS/L |
| | Anhydrous citric acid | 0.11 g/L |
| | Trisodium citrate dihydrate | 1.37 g/L |
| | Water | |
| pH | | 6.3 |
| Temperature | | 50° C. |
| Volume of reaction tank | | 5 L |
| Amount of reaction solution | | 2.4 L |
| Stirring rate | | 200 rpm |
| Reaction time | | 48 hours |

After completion of the reaction, without performing the deactivation treatment of CGTase, and using an ultrafiltration membrane (a molecular weight cut-off 6000: SIP-1013, a molecular weight cut-off 13,000: ACP-1010D, and a molecular weight cut-off 50,000: AHP-1010, manufactured by Asahi Kasei Corporation), cross-flow ultrafiltration was performed under respective conditions shown in Table 2. A method of ultrafiltration was as follows. A diluted solution obtained by adding 3.0 L of water to 2.2 L of the reaction solution was added to a stock solution tank of a membrane device in which an ultrafiltration membrane was placed. A circulation pump was operated to concentrate the stock solution to 1.1 L while circulating it, and the filtrate was recovered. Thereafter, a step of adding 1 L of water to the stock solution tank and further recovering the filtrate was repeated 5 times. All the filtrates were mixed, and thereby 9.1 L of a recovered filtrate was obtained. Accordingly, inositol derivatives were recovered in the filtrate, and CGTase remaining in a concentrate was separated off and removed.

After the ultrafiltration, the activity of residual CGTase in the filtrate was checked.

In addition, in order to evaluate coloration and alteration of the inositol derivatives, which are reaction products, and the presence of soluble peptides derived from CGTase, OD660, OD440, and OD280 per 1 g of a solid content of the filtrate after the ultrafiltration were measured. In the same manner, OD660, OD440, and OD280 per 1 g of a solid content of the reaction solution before the ultrafiltration were measured.

In addition, the analysis of main components in the reaction solution before the ultrafiltration and the filtrate after the ultrafiltration was performed to evaluate a composition change of the inositol derivatives which is a main component. The number of peaks detected by liquid chromatography, a retention time of each peak, and an area proportion of each peak were compared between the two samples, and in a case where the number of peaks and the retention time of each peak matched between the two samples, and a difference in the area proportion of each peak between the two samples was within 10% of a value detected in the reaction solution before the ultrafiltration (100%), a composition change of the main component was determined as "no change."

The results are shown in Tables 2 and 3. In Tables 2 and 3, a "reaction solution" indicates a reaction solution after the inositol derivatives generation reaction and before the ultrafiltration, and a "filtrate" indicates a filtrate after the ultrafiltration. A "treatment time" indicates a time taken to obtain a recovered filtrate in which all the filtrates had been mixed.

After completion of the reaction, CGTase was subjected to deactivation treatment and separation treatment under the conditions shown in Tables 4 and 5. In each separation treatment in Tables 4 and 5, treatment using an ultrafiltration membrane was performed in the same manner as in Examples 1 to 7. Centrifugal filtration was performed using a basket-type centrifugal filter (a small centrifugal separator H-110A, a filter cloth model: Cotton 26, manufactured by KOKUSAN Co., Ltd.) in which a filter cloth is used as a filter medium. Microfiltration was performed using a microfiltration membrane (PSP-113) manufactured by Asahi Kasei Corporation.

TABLE 2

|  |  | Example 1 | Example 2 | Example 3 | Example 4 |
|---|---|---|---|---|---|
| Ultrafiltration conditions |  |  |  |  |  |
| Molecular weight cut-off of ultrafiltration membrane |  | 6000 | 6000 | 6000 | 6000 |
| Temperature |  | 10° C. | 20° C. | 30° C. | 40° C. |
| Treatment time |  | 1.2 hours | 1.0 hours | 1.0 hours | 1.0 hours |
| Evaluation |  |  |  |  |  |
| OD660 (Turbidity) | Reaction solution | 0.20 | 0.20 | 0.20 | 0.20 |
|  | Filtrate | 0.008 | 0.008 | 0.008 | 0.008 |
| OD440 (Coloration) | Reaction solution | 0.024 | 0.024 | 0.024 | 0.024 |
|  | Filtrate | 0.013 | 0.013 | 0.013 | 0.013 |
| OD280 (Soluble peptide) | Reaction solution | 4.2 | 4.2 | 4.2 | 4.2 |
|  | Filtrate | 3.6 | 3.6 | 3.6 | 3.6 |
| Activity of residual CGTase in filtrate |  | No activity | No activity | No activity | No activity |
| Composition change of main component of filtrate |  | No change | No change | No change | No change |

TABLE 3

|  |  | Example 5 | Example 6 | Example 7 |
|---|---|---|---|---|
| Ultrafiltration conditions |  |  |  |  |
| Molecular weight cut-off of ultrafiltration membrane |  | 6000 | 13000 | 50000 |
| Temperature |  | 50° C. | 20° C. | 20° C. |
| Treatment time |  | 1.0 hours | 1.0 hours | 1.0 hours |
| Evaluation |  |  |  |  |
| OD660 (Turbidity) | Reaction solution | 0.20 | 0.20 | 0.20 |
|  | Filtrate | 0.008 | 0.008 | 0.008 |
| OD440 (Coloration) | Reaction solution | 0.024 | 0.024 | 0.024 |
|  | Filtrate | 0.019 | 0.013 | 0.016 |
| OD280 (Soluble peptide) | Reaction solution | 4.2 | 4.2 | 4.2 |
|  | Filtrate | 3.7 | 3.6 | 3.8 |
| Activity of residual CGTase in filtrate |  | No activity | No activity | No activity |
| Composition change of main component of filtrate |  | No change | No change | No change |

Based on the results shown in Tables 2 and 3, it was confirmed that CGTase activity in the filtrate was eliminated by performing ultrafiltration after inositol derivatives generation reaction. In addition, based on the results of the analysis of main components and the measurement of absorbance, it was confirmed that inositol derivatives with a high degree of purification was obtained without altering the inositol derivatives.

Comparative Examples 1 to 8

Under the conditions shown in Table 1, myo-inositol was reacted with β-cyclodextrin in the presence of CGTase, and thereby inositol derivatives were generated.

Thereafter, in the same manner as in Examples 1 to 7, the activity of residual CGTase in the filtrate after the deactivation treatment and separation treatment was measured.

In addition, OD660, OD440, and OD280 with respect to solid contents of the filtrate after the separation treatment were measured. In the same manner, OD660, OD440, and OD280 per 1 g of a solid content of the reaction solution before the deactivation treatment and separation treatment were measured.

In addition, the analysis of main components in the reaction solution before the deactivation treatment and separation treatment and the filtrate after the deactivation treatment and separation treatment was performed to evaluate a composition change of the inositol derivative which is a main component. Criteria for determining a composition change of the main component as "no change" were the same as those in Examples 1 to 7.

The results are shown in Tables 4 and 5. In Tables 4 and 5, the letter "MW" indicates a molecular weight cut-off. A "reaction solution" indicates a reaction solution after the deactivation treatment and before the separation treatment for Comparative Examples 1 to 6, and indicates a reaction solution before the separation treatment after the inositol derivatives generation reaction for Comparative Examples 7 and 8. A "filtrate" indicates a filtrate after the separation treatment.

treatment. In addition, all values of OD440 (coloration) of Comparative Examples 1 to 8 were higher as compared with those of Examples 1 to 7. In Comparative Examples 2, 4, 6, and 7, values of OD660 (turbidity) were also higher as compared with those of Examples 1 to 7, and in Comparative Examples 2, and 4 to 8, values of OD280 (soluble peptide) were also higher as compared with those of Examples 1 to 7. Furthermore, in a case where centrifugal filtration or microfiltration was performed instead of the ultrafiltration (Comparative Examples 7 and 8), CGTase activity in the filtrate was still observed. Based on the above results, it was confirmed that CGTase cannot be removed by

TABLE 4

|  |  | Comparative Example 1 | Comparative Example 2 | Comparative Example 3 | Comparative Example 4 |
|---|---|---|---|---|---|
| Conditions for deactivation treatment | | 120° C. 10 minutes | 120° C. 10 minutes | Addition of HCl pH 1 | Addition of HCl pH 1 |
| Conditions for separation treatment | | | | | |
| Type of separation treatment | | Ultra-filtration membrane (MW6000) | Centrifugal filtration (filter cloth: Cotton 26) | Ultra-filtration membrane (MW6000) | Centrifugal filtration (filter cloth: Cotton 26) |
| Temperature | | 20° C. | 20° C. | 20° C. | 20° C. |
| Treatment time | | 1.0 hours | 0.3 hours | 1.0 hours | 0.3 hours |
| Evaluation | | | | | |
| OD660 | Reaction solution | 0.35 | 0.35 | 0.29 | 0.29 |
| (Turbidity) | Filtrate | 0.008 | 0.15 | 0.008 | 0.20 |
| OD440 | Reaction solution | 0.045 | 0.045 | 0.038 | 0.038 |
| (Coloration) | Filtrate | 0.028 | 0.045 | 0.022 | 0.038 |
| OD280 | Reaction solution | 4.1 | 4.1 | 4.1 | 4.1 |
| (Soluble peptide) | Filtrate | 3.5 | 4.1 | 3.6 | 4.1 |
| Activity of residual CGTase in filtrate | | No activity | No activity | No activity | No activity |
| Composition change of main component of filtrate | | Changed | Changed | Changed | Changed |

TABLE 5

|  |  | Comparative Example 5 | Comparative Example 6 | Comparative Example 7 | Comparative Example 8 |
|---|---|---|---|---|---|
| Conditions for deactivation treatment | | Addition of NaOH pH 12 | Addition of NaOH pH 12 | No treatment | No treatment |
| Conditions for separation treatment | | | | | |
| Type of separation treatment | | Ultra-filtration membrane (MW6000) | Centrifugal filtration (filter cloth: Cotton 26) | Centrifugal filtration (filter cloth: Cotton 26) | Micro-filtration (cutoff: 0.1 μm) |
| Temperature | | 20° C. | 20° C. | 20° C. | 20° C. |
| Treatment time | | 1.0 hours | 0.3 hours | 0.3 hours | 0.3 hours |
| Evaluation | | | | | |
| OD660 | Reaction solution | 0.18 | 0.18 | 0.20 | 0.20 |
| (Turbidity) | Filtrate | 0.008 | 0.09 | 0.09 | 0.008 |
| OD440 | Reaction solution | 0.039 | 0.039 | 0.024 | 0.024 |
| (Coloration) | Filtrate | 0.023 | 0.039 | 0.024 | 0.024 |
| OD280 | Reaction solution | 4.5 | 4.5 | 4.2 | 4.2 |
| (Soluble peptide) | Filtrate | 4.1 | 4.5 | 4.2 | 4.2 |
| Activity of residual CGTase in filtrate | | No activity | No activity | Activity | Activity |
| Composition change of main component of filtrate | | Changed | Changed | Changed | Changed |

As shown in Tables 4 and 5, in Comparative Examples 1 to 8, a composition change of the main component was observed after the deactivation treatment and separation filtration methods other than the ultrafiltration. In addition, the results show that, in a case where the deactivation treatment was performed, inositol derivatives were altered, and coloration or the like could not be removed even after the separation treatment was performed.

INDUSTRIAL APPLICABILITY

According to the present invention, a method for producing an inositol derivative is provided by which a high-quality inositol derivative with a high degree of purification can be obtained.

The invention claimed is:

1. A method for producing an inositol derivative, comprising:
a step of reacting inositol and dextrin in the presence of cyclodextrin glucanotransferase to generate an inositol derivative in which a sugar is bonded to the inositol, and to obtain a solution containing the inositol derivative and the cyclodextrin glucanotransferase; and
a step of removing the cyclodextrin glucanotransferase in the solution using an ultrafiltration membrane,
wherein a deactivation treatment of the cyclodextrin glucanotransferase in the solution is not performed, and the dextrin is β-cyclodextrin.

2. The method for producing an inositol derivative according to claim 1, wherein a molecular weight cut-off of the ultrafiltration membrane is 1,000 to 100,000.

3. The method for producing an inositol derivative according to claim 1, wherein the removal of the cyclodextrin glucanotransferase using the ultrafiltration membrane is performed under a temperature condition of 0° C. to 60° C.

4. The method for producing an inositol derivative according to claim 1, wherein the removal of the cyclodextrin glucanotransferase using the ultrafiltration membrane is performed by cross-flow ultrafiltration.

5. The method for producing an inositol derivative according to claim 1, wherein the reaction of reacting the inositol with the dextrin is performed under a condition in which a temperature is 20° C. to 80° C. and a pH is 3 to 9.

6. The method for producing an inositol derivative according to claim 1, wherein the inositol is myo-inositol.

7. The method for producing an inositol derivative according to claim 2, wherein a molecular weight cut-off of the ultrafiltration membrane is 1,000 to 70,000.

* * * * *